United States Patent [19]

Fenton, Jr.

[11] Patent Number: 5,178,612
[45] Date of Patent: Jan. 12, 1993

[54] COMPRESSIBLE SPLIT CYLINDER BAYONET LOCKING DEVICE FOR ATTACHMENT OF A CATHETER TO A FLUID TRANSFER DEVICE

[75] Inventor: Paul V. Fenton, Jr., Marblehead, Mass.

[73] Assignee: Strato Medical Corporation, Beverly, Mass.

[21] Appl. No.: 595,036

[22] Filed: Oct. 10, 1990

[51] Int. Cl.⁵ ............................ A61M 25/00
[52] U.S. Cl. .................... 604/283; 604/175; 285/158; 285/242; 285/419
[58] Field of Search .............. 604/175, 240, 242, 243, 604/283, 905; 128/912; 285/158, 189, 360, 361, 373, 376, 396, 401, 402, 419, 239, 242

[56] References Cited

U.S. PATENT DOCUMENTS

| | | | |
|---|---|---|---|
| 3,853,126 | 12/1974 | Schulte | 604/175 |
| 4,006,744 | 2/1977 | Steer | 128/214 R |
| 4,013,310 | 3/1977 | Dye | 285/110 |
| 4,405,312 | 10/1983 | Gross et al. | 604/283 |
| 4,673,394 | 6/1987 | Fenton, Jr. et al. | 604/175 |
| 4,675,007 | 6/1987 | Terry | 604/283 |
| 4,723,948 | 2/1988 | Clark et al. | 604/905 |
| 4,733,666 | 3/1988 | Mercer, Jr. | 128/346 |
| 4,752,292 | 6/1988 | Lopez et al. | 604/244 |
| 4,762,517 | 8/1988 | McIntyre et al. | 604/175 |
| 4,772,276 | 9/1988 | Wiita et al. | 604/283 |
| 4,790,829 | 12/1988 | Bowden et al. | 640/244 |
| 4,796,615 | 1/1989 | Bullock et al. | 128/202.27 |
| 4,880,414 | 11/1989 | Whipple | 604/283 |

FOREIGN PATENT DOCUMENTS 1554470 2/1968 France .

Primary Examiner—John D. Yasko
Assistant Examiner—Anthony Gutowski
Attorney, Agent, or Firm—Lahive & Cockfield

[57] ABSTRACT

A bayonet twist locking connector is disclosed for detachably securing an end of a catheter to a fluid transfer device including a flange defining a T-shaped opening for receiving the device and a fluid port extending outwardly along a central axis of the opening. The connector includes a split resilient body which defines an aperture for receiving an end of the catheter. The body being split allows the aperture to be enlarged to facilitate insertion of the catheter. The connector further includes a bayonet assembly for twist locking the connector in the opening of the fluid transfer device, and complementary wing elements radially projecting adjacent to the slit for clamping together and against a region of the fluid transfer device. So clamping the complementary wings prohibits the connector from being removed from the opening, and generates a compressive force to secure the catheter to the port of the fluid transfer device.

16 Claims, 2 Drawing Sheets

COMPRESSIBLE SPLIT CYLINDER BAYONET LOCKING DEVICE FOR ATTACHMENT OF A CATHETER TO A FLUID TRANSFER DEVICE

BACKGROUND OF THE INVENTION

The present invention generally relates to the field of catheter assemblies for providing a treatment material, such as a drug in fluid form, directly to the vascular system of a mammal. In particular, the invention relates to a device for releasably attaching an end of a catheter to a vascular access port, or other device.

Numerous surgical and non-surgical treatment procedures require that a catheter be placed in fluid communication with a patient's vascular system. A number of devices for this purpose are known. Both implantable treatment reservoirs, such as disclosed in U.S. Pat. No. 4,673,394, and traditional cannula devices afford access to a patient's vascular system, using catheters attached to those devices.

In the prior art, catheters are typically permanently affixed to the implantable device prior to implantation.

It is also known to use an implantable device together with a catheter which are adapted for attachment to a port of that device during the implantation procedure, but after the device is positioned within the patient. Typically, such catheters are adapted to be slidingly placed over a tubular port of the device, and frictionally held in place. Due to the nature of the procedures by which implantable treatment devices are surgically implanted in patients, it is necessary that the connection between a catheter and the implantable device be easily accomplished. This enables a surgeon to concentrate on the proper placement of the implantable device. The friction fit placement of catheters has proved to be very difficult in practice.

While such configurations provide a secure connection, they are undesirable because the permanent connection restricts the degree to which the implantable device can be manipulated, thereby making installation cumbersome. As a result, optimum placement of the implantable device is often achieved only with great difficulty, or sometimes not at all achieved.

Known connectors comprising a mere collar circumscribing the catheter which fits over a male tube projecting from the implantable device often do not afford secure attachment. If the inner diameter of the collar does not properly correspond to the outer diameter of the catheter, either the collar will not fit over the catheter, or the collar will not generate a sufficient compressive force to secure the catheter to the exit port. With known assemblies, therefore, it is necessary to keep on hand a variety of connectors so that a connector can be used which is specifically designed for use with the particular catheter being connected.

U.S. Pat. No. 4,673,394 discloses a particularly effective device for attaching a catheter to an implanted access port. That device is a twist-lockable (bayonet-type) coupler in which a pair of bayonet pins extend in opposite directions from the generally cylindrical outer surface of the coupler. The pins, together with the geometry of the coupler may be slidingly positioned over the tubular port of an access device with a particular angular orientation, and then twisted so that the pins are captively held in place by the portions of the implantable device which defines a void region used to capture the pins.

One problem for this coupler is that the surgeon might encounter difficulty exactly matching the inner diameter of the coupler with the outer diameter of the catheter when it is positioned over the tubular port. Such difficulty would result in corresponding difficulty in attaching the catheter to the port. Moreover, the bayonet coupler must be manually held in place during and until it is sutured in place by the surgeon.

It is, therefore, an object of the present invention to provide an improved connector that will securely attach a catheter to an implantable device.

It is another object to provide a catheter-to-implantable device connector which is easily installed.

It is yet another object of the invention to provide such a connector which can be utilized with a variety of catheters having different diameters.

SUMMARY OF THE INVENTION

The problems associated with known catheter connectors are greatly resolved by the present invention which is a compressible split cylinder bayonet locking device for easily and securely attaching a catheter to an implantable device. The invention includes a split body which enables the invention to be easily installed and also to connect securely to an implantable device. The invention permits the use of a variety of catheters having different outer diameters with a single coupler.

One form of the invention is adapted for use with an implantable device such as that described in U.S. Pat. No. 4,673,394. That implantable device includes a tubular port extending from its periphery, where that port is surrounded by a generally T-shaped void region defined by a peripheral flange.

In accordance with this form of the invention, a longitudinally extending, resilient coupler body defines a central, axially extending aperture for receiving a catheter. The body is split along one side parallel to its longitudinal axis. This, in conjunction with the fact that the body is formed of a resilient material, enables the body to be deformed in a hinged manner to enlarge the central aperture to facilitate insertion of the catheter into the aperture, and connection of the inserted catheter onto the tubular exit port extending from the implantable device.

Bayonet capture pins radially project from an end of the body distal to the catheter. The bayonet capture pins allow the connector to be slidingly placed over the tubular port in a first orientation about the longitudinal axis of the connector and then rotated about that axis to a "locked" position with the bayonet pins captively positioned within the T-shaped void region of the implantable device. When the connector is rotationally displaced to the locked orientation, the bayonet capture pins, in cooperation with the portion of the port that defines the opening, prohibit the connector from being removed from the tubular exit port of the implantable device.

In a preferred embodiment, opposed wings radially project from each side of the coupler body adjacent to the slit. The wings are adapted to be clamped together and against the flange of the implantable device to close the slit, thereby compressing the catheter end against the tubular port and securing the coupler in its locked position to the implantable device. In use therefore, a catheter is inserted into the central aperture while the coupler body is deformed to enlarge the central aperture sufficiently to readily receive the catheter. Then, the coupler, together with the catheter, are slidingly placed onto the tubular port of the implantable device, and the connector is properly twist locked to bring the bayonet pins into captive engagement. The wings on the body are then clamped together, thereby transmitting a compressive force to secure the catheter to the port. The wings are preferably clamped together, for example, by suturing, in such a manner affixing them to the implantable device so that the connector cannot be inadvertently rotated. This prevents the catheter from being detached from the port of the implantable device.

In one form of the invention, the implantable device includes a flange which defines the T-shaped void region used to capture the bayonet pins. In the preferred form, the flange extends radially outward from the peripheral surface of the implantable device. A resilient clamp tab projects up from the flange. The clamp tab includes a portion adapted to clamp the pressed-together wings of the connector against the flange. The connector is formed so that when the wings are in a position to be clamped by the clamp tab, the connector is rotationally displaced (from its inserting orientation) to its locked position, so that when the wings are clamped, the connector cannot be removed from the opening. In an alternate embodiment of the invention, the wings define an opening by which, in addition to, or in place of, being clamped by the tab, they can be sutured to the flange of the implantable device. So doing will provide additional security that the catheter will not be inadvertently detached from the port.

BRIEF DESCRIPTION OF THE DRAWING

These and other advantages of the invention will be more fully understood by reference to the following detailed description in conjunction with the attached drawing in which like reference numerals refer to like elements and in which.

DETAILED DESCRIPTION OF PREFERRED EMBODIMENTS

The present invention is a compressible split cylinder bayonet locking connector for securely attaching a catheter to an implantable device. The connector includes a generally cylindrical, coupler body defining a substantially cylindrical central aperture extending along a central axis, for receiving the catheter at one end and a tubular port of the implantable device at the other end. The connector further includes portions of a bayonet lock for securing the connector to the implantable device, and a pair of opposed wing elements projecting substantially radially from the coupler body to enable the compressive securing of the catheter to the tubular port of the implantable device. The connector is split along one side to enable the coupler body to be resiliently hinged about a hinge axis substantially parallel to its central axis to enlarge the central aperture for receiving catheters of different thicknesses. In this form of the invention, when the opposed wing elements are biased together, a compressive force is generated to secure the catheter to the outer surface of the tubular port of the implantable device.

Figure 1:
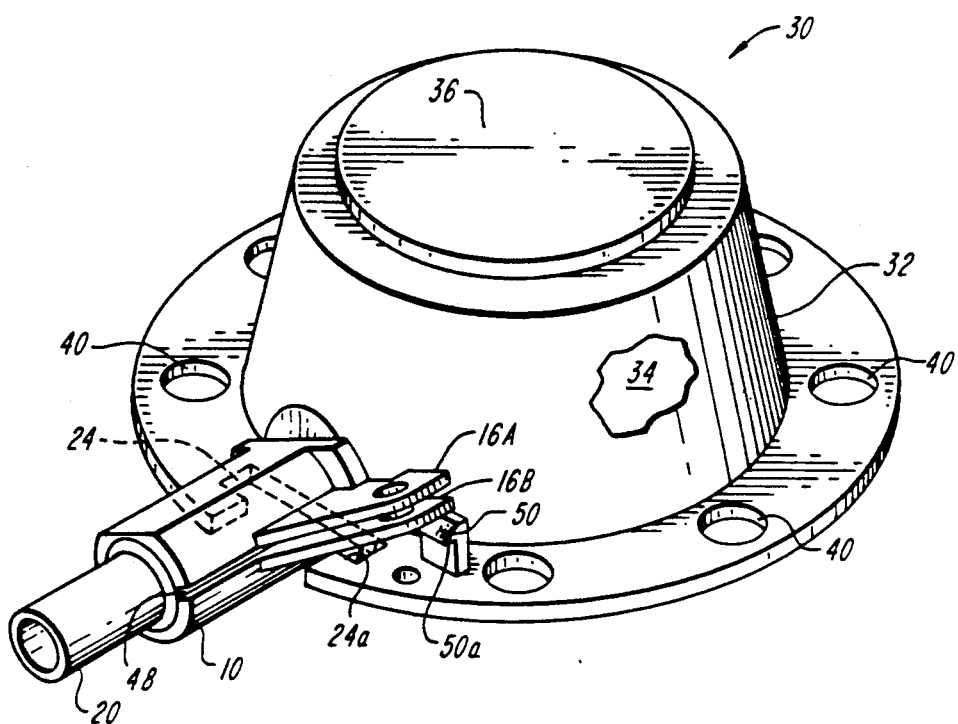
FIG. 1 is a perspective view of a catheter connector constructed in accordance with the present invention shown just prior to being twist locked to secure a catheter to an implantable device.

FIG. 1 shows a perspective view of a connector 10, embodying the invention, about to secure the proximal end of a flexible vascular catheter 20 to an implantable device 30. The distal end (not shown) of the catheter 20 is positioned at a desired position in the patient's vascular system.

Figure 2:
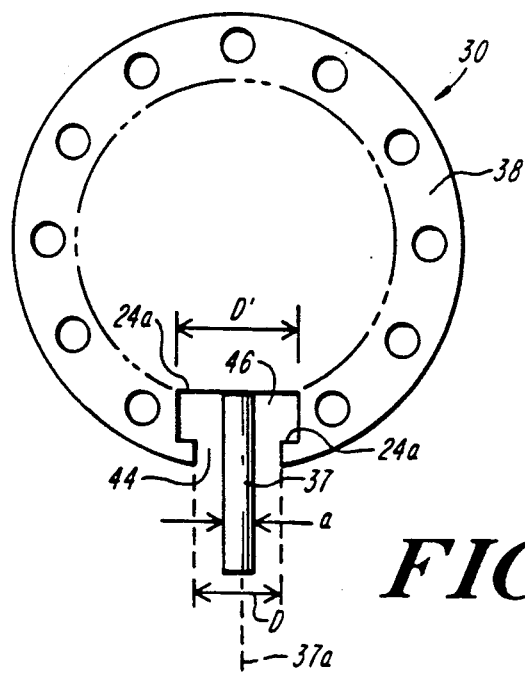
FIG. 2 is a bottom view of an implantable device used in conjunction with the connector of the present invention.

The device 30 includes a housing 32 defining an internal generally cup-shaped recess forming a reservoir cavity 34, e.g. for holding treatment fluids or medicine. The housing 32 has an open face which is closed off by a cover 36. The cover 36 is formed of a self-resealing polymer, which is preferably an elastomer such as silicon, rubber or latex, and is adapted to permit access to the reservoir cavity 34 using a hypodermic needle. FIG. 2 shows a bottom view of the device 30 only, showing a tubular port 37 (having outer diameter a) extending along a port axis 37a from the housing 32. The interior of port 37 is coupled directly to the cavity 34.

The housing 32 is formed of a biocompatible material such as electro polished 316L stainless steel or other surgical grade steel or biocompatible hard material, such as titanium, DuPont Delrin TM (acetal resin) or Teflon TM (polytetrafluoroethylene), Nylon, polyethylene thermoplastic, or mixtures thereof.

A substantially planar, radially extending flange 38 circumscribes the housing 32 of access port 30. The flange 38 includes an array of holes 40 evenly spaced about the perimeter of the housing 32, for use in suturing the device 30 to a layer of the patient's tissue during the implantation procedure.

In use, a hypodermic needle may be used to puncture the cover 36 to deliver a treatment fluid to the reservoir cavity 34. The treatment fluid is then delivered to the catheter 20 coupled to the tubular exit port of the device 30, in a manner described below, whereby it is provided to the vascular system of the patient. The device 30 may alternatively be configured to permit out-flow of body fluids, for example, blood in conjunction with a hemodialysis procedure.

Because the device 30 is intended to be sutured directly to the patient, a high degree of maneuverability of the device 30 and accessibility of the suture holes 40 is desired to facilitate the surgical process of implantation. Additionally, because the device 30 connects directly, via the catheter 20, to the patient's vascular system, the integrity of the connection between the catheter 20 and the device 30 must be assured. Moreover, in order to reduce risk of harm to the patient, it is preferred that the catheter be moved minimally during and after placement of the distal tip within the vascular system.

Toward these ends, it is desirable to first position and affix the device 30, then insert the distal tip of the catheter to the desired location, and finally size the length of the catheter 20 by cutting the proximal end and sliding that proximal end over the tubular port of the device 30. The coupling of catheter 20 to device 30 is accomplished by the twist lockable connector 10. Connector 10 is adapted to receive catheters having a range of outer diameters and simply and securely affix them to the implantable device 30. It is an important feature of the invention, that means are provided for safely securing the connector against rotation so that it can not be inadvertently detached from the implantable device.

As shown in FIG. 2, the flange 38 defines a T-shaped opening, or void region 24 disposed about the tubular port 37. In FIG. 2, the void region 24 comprises an axially extending portion 44 and a circumferentially extending portion 46. The axial portion 44 has a width D and the circumferential portion 46 has a width D' where D' is greater than D. It should be understood that in the context of the invention, "T-shaped" refers to any reasonable shape having a width on the perimeter of the flange 38 which is smaller than the width at the end of the void region 24 which is distal to the flange perimeter. An alternate example of such an opening would be a dovetail-shaped opening.

Figure 3A:
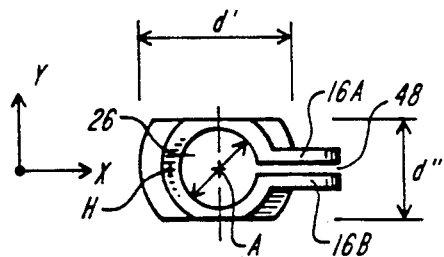
FIGS. 3A through 3C are orthogonal plan views of the connector of the present invention.
Figure 3B:
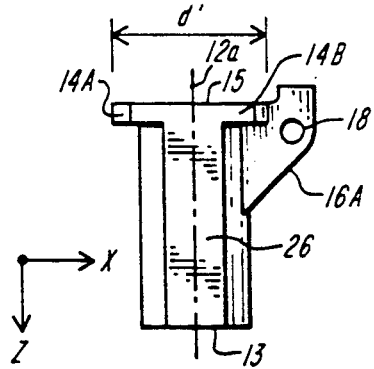
Figure 3C:
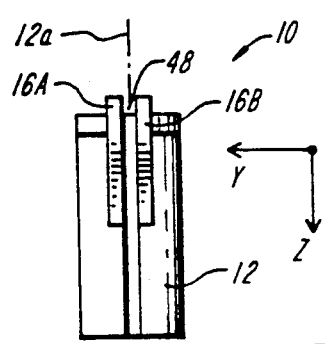

FIGS. 3A–3C show end, top, and side elevation views, respectively of the connector 10, with respect to orthogonal X, Y, and Z axes. The connector 10 includes a generally cylindrical, elongated coupler body 12 extending in the z-direction along an axis 12a. Bayonet portions (or pins) 14A and 14B extend outward (with respect to axis 12a) from body 12 in substantially one (X) direction only to establish a general T-shape (having width d' in the x-direction) to connector 10 in the view shown in FIG. 3B, but a general linear shape (having width d in the y-direction) to connector 10 in the view shown in FIG. 3C. The width d is less than D and the width d' is greater than D, but less than D'. The coupler body 12 defines a generally cylindrical central aperture 26 having diameter A.

The coupler body 12 includes a slit 48 which longitudinally splits body 12 to establish a gap extending along the entire length of the central aperture. A pair of opposed wing elements 16A and 16B extend radially outward (substantially in the x direction as shown) from the respective edges of the body 12 at the edges of slit 48. The device 10 may be constructed from a resiliently, deformable material, such as polyoxymethylacrylate. With such a construction, the slit 48 establishes a hinge region in body 12 generally opposite the slit. The hinge region permits hinge-like deformation of the body 12 about a hinge axis H to enlarge the central aperture 26 for easily receiving the catheter 20 and for reducing the aperture 26 to compress the proximal end of catheter 20 about the outer surface of the tubular port 37 of device 30. In the illustrated embodiment, the hinge region is distributed over a relatively large angular segment of body 12. In other embodiments, the hinge region, or flexure, may be more localized, for example, by placing an axially extending groove along a surface of the central aperture opposite slit 48.

The connector 10 is sized so that when a catheter is inserted into the aperture 26, the walls defining the split 48 will be slightly urged apart with accompanying deformation about the hinge axis. In this manner, by clamping the opposed wing elements 16A and 16B to one another, a compressive force can be generated to act on the catheter 20, and compressively secure the catheter to the port 37.

The connector 10 is adapted to clamp the flexible catheter 20 to port 37, where the nominal inner diameter of catheter 20 is less than a and the nominal outer diameter of catheter 20 is greater than A when the catheter is extended to have its inner diameter equal to a (e.g. when the catheter is positioned on port 37).

With the above-described configuration, following placement of the catheter 30 over the tubular port 37, the connector 10 may be placed over the catheter and angularly oriented so that its narrow (dimension d) portion of the connector 10 and catheter 20 can be slidably positioned over port 37 and into the T-shaped void region 24. Once the pins 14A and 14B of connector 10 has been inserted fully into the void region 24 so that the back 15 abuts the housing 32, the connector 10 may be rotated about its longitudinal axis. Thus, when the connector 10 is moved axially into the opening 24 and butted up against the housing 32, rotation of the connector 10 within the void region 24 captures the connector 10 within the T-shaped opening 24 in the manner of a bayonet mount to prevent axial motion thereof.

Figure 4:
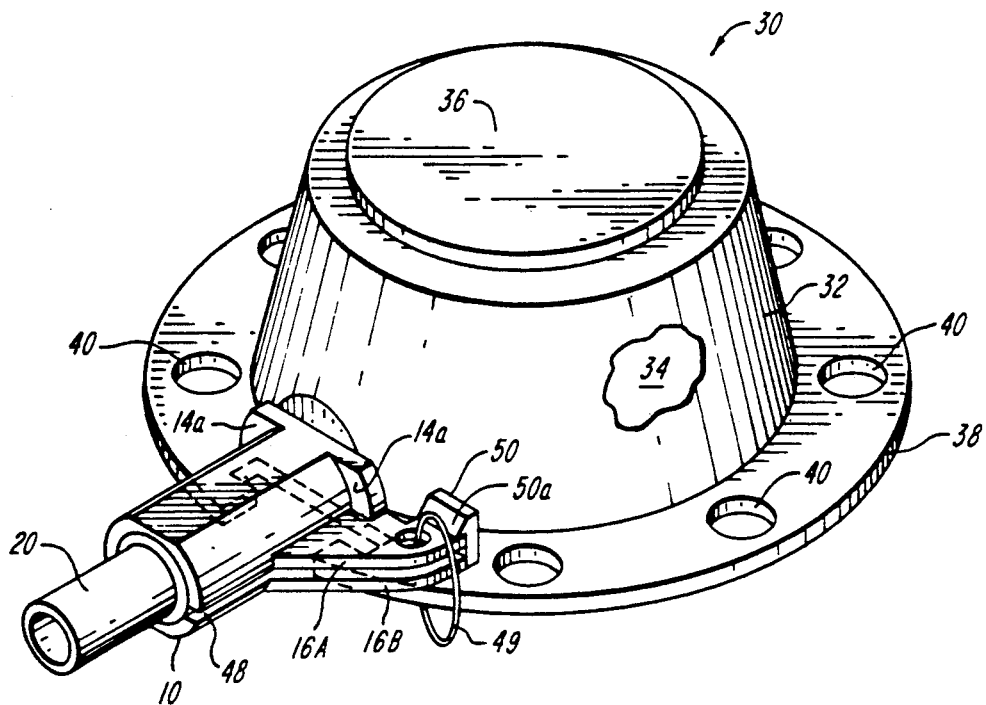
FIG. 4 is a perspective view of a connector in accordance with the present invention shown in its locked orientation.

FIG. 4 shows the connector 10 locked in place in the T-shaped opening 24 of the flange 38 to secure a catheter 20 to the implantable device 30. The complementary wing elements 16A and 16B are held in place against the flange 38 by a suture 49.

The illustrated embodiment also includes an optional resilient clamp tab 50 extending upward from flange 38 and including a lip portion 50a. The clamp tab 50 is positioned so that as the wings 16A and 16B are moved toward flange 38, those wings initially deflect tab 50 and then become captively engaged by lip 50a as tab 50 returns to its original position. At this point, tab 50 clamps wings 16A and 16B together as well as securing them to the flange 38.

By clamping the wings 16A and 16B together, the tab 50, via the body 12 of the connector 10, will apply a compressive force to secure the catheter 20 to the tubular port 37. Also by preventing the connector 10 from being rotated, the snap-down tab 50 is able to lock the connector 10 in position. As a result, the catheter 20 cannot be inadvertently removed from the exit port 37. As an additional security measure, the complimentary wings 16A and 16B are sutured to the flange 38.

In an alternate embodiment of the invention, if catheters of a single consistent outer diameter are to be used, the connector 10 can be formed as a contiguous body. That is, no split is used. This embodiment of the invention still offers advantages over known connectors through the cooperation of the wings 16A and 16B with the snap-down device 50 which provides a secure connection between the catheter 20 and the implantable device 30.

As discussed above, it will be appreciated that other forms of twist lock coupling of a catheter to the housing are possible and that for a given bayonet structure, the corresponding opening on the flange may be fabricated. According to the principle of one aspect of the invention, the housing includes an exit port extending from its reservoir and a mounting means on the exit port adapted to receive a mating twist lock catheter connection. The specific details of the mounting means of the housing, however, will vary according to selected bayonet coupling.

Moreover, the invention may be used for extracorporeal applications, where the fluid transfer device may be other than an implantable device. For example, the connector 10 may be used to connect with a device having a suitable T-shaped opening extending about a tubular fluid flow port.

It will be understood therefore, that the above description pertains to but two of several embodiments of the present invention. That is, description is intended as illustrative rather than limiting. The invention, therefore, is to be defined not by the preceding description but by the claims that follow.

What is claimed is:

1. Connector apparatus for coupling an end of a resilient tube about the exterior of a tubular extension of a fluid transfer assembly, said extension extending along a port axis and having an outer diameter a, comprising:
 a resilient body member having a substantially cylindrical central aperture extending along a central axis, said aperture having a diameter A, where A is greater than a, said body member including:
  A. a split extending along one side of said central aperture and defined by opposed edges of said body member,
  B. a distributed hinge region adjacent to said central aperture opposite said slit and extending along a hinge axis, said hinge axis being parallel to said central axis, said hinge region separating said body part into a first portion and a second portion and permitting deformation of the resilient body member to enlarge the central aperture and thereby facilitate insertion of a resilient tube into the central aperture, and,
  C. compression means including force-receiving elements extending outward from points near said slit edges for receiving external forces to bias said edges of said slit toward each other for reducing the central aperture to compress the resilient tube about a tubular extension of a fluid transfer assembly.

2. The connector apparatus of claim 1 wherein said body member further includes:
 bayonet means responsive to coaxial alignment of said port axis and said central axis and to subsequent rotation of said first portion of said body member about said hinge axis toward said second portion of said body member, for selectively engaging said body member to said fluid transfer assembly with said aperture being coaxial with and positioned about said tubular extension.

3. The connector apparatus of claim 1 wherein the norminal inner diameter of said tube is less than a and the norminal outer diameter of said tube is greater than A when said tube is extended to have an inner diameter equal to a,
 wherein said body member has means for engaging said fluid transfer assembly and is adapted to captively hold said tube end to said tubular extension when said body part is engaged to said fluid transfer assembly.

4. The connector apparatus of claim 2 wherein the nominal inner diameter of said tube is less than a and the nominal outer diameter of said tube is greater than A when said tube is extended to have an inner diameter equal to a,
 wherein said body member is adapted to captively hold said tube end to said tubular extension when said body part is engaged to said fluid transfer assembly.

5. The connector apparatus of claims 1 or 2 or 4 wherein said compression means includes a first substantially planar wing element extending radially from said slit edge of said first portion and a second substantially planar wing element extending radially from said slit edge of said second portion.

6. The connector apparatus of claim 5 further comprising in combination with said body member, said fluid transfer assembly, said fluid transfer assembly including means for selectively capturing said wing elements against said fluid transfer assembly when said body member is engaged to said fluid transfer assembly with said aperture being coaxial with and positioned about said tubular extension and said opposed edges of said slit are positioned substantially adjacent to each other.

7. The connector apparatus of claim 6 wherein said capture means includes a resilient capture member extending from said fluid transfer assembly adapted to captively engage said wing elements when said elements are positioned against a reference location on said fluid transfer assembly.

8. A locking connector for securing an end of a catheter to a fluid transfer device including a T-shaped opening extending inwardly along a port axis from the periphery of said device, said device including a tubular port extending within said T-shaped opening and along said port axis, said T-shaped opening having a minimum width D and a maximum width D' in the direction transverse to said port axis, said connector comprising:
 a resilient body extending along a central axis and including a bayonet portion having a maximum outer dimension less than D in a first direction transverse to said central axis and a maximum outer dimension d' in a second direction transverse to said central axis, said second direction being orthogonal to said first direction, said body defining a substantially cylindrical aperture coaxial with said central axis for receiving the end of the catheter and a split parallel to said longitudinal axis, said split allowing said body to be resiliently deformed to enlarge said aperture thereby facilitating insertion of the catheter into said aperture;
 whereby said bayonet is adapted for registration with the T-shaped opening, so that said connector is freely insertable into the opening when the connector is in a first orientation and not insertable or removable from the opening when the connector is in a second orientation rotationally displaced from said first orientation; and
 said body further including complementary wing elements adjacent to said split and extending radially therefrom with respect to said central axis;
 said wing elements being adapted for being biased together and clamped against a region of said fluid transfer device, thereby applying a compressive force to reduce the central aperture and thereby secure the catheter to the tubular port while preventing said connector from rotating about said central axis.

9. An implantable assembly comprising:
A. a fluid transfer device including:
 a housing defining a reservoir for a fluid;
 a flange at least partially circumscribing said housing and defining a T-shaped opening having a minimum width D;
 a fluid port extending outwardly along a port axis of said T-shaped opening for providing a flow channel from said reservoir to the distal tip of said port; and
B. a connector for detachably securing a catheter to said port of said fluid transfer device, said connector including:
 a resilient body extending along a central axis and including a bayonet portion having a maximum outer dimension less than D in a first direction transverse to said central axis and a maximum outer dimension D' in a second direction transverse to said central axis, said second direction being orthogonal to said first direction, said body defining a substantially cylindrical aperture coaxial with said central axis for receiving the end of the catheter and a split parallel to said central axis, said split allowing said body to be resiliently deformed to enlarge said aperture thereby facilitating insertion of the catheter into said aperture;

whereby said bayonet portion is adapted for registration with the T-shaped opening, so that said connector is freely insertable into the opening when the connector is in a first orientation and not insertable or removable from the opening when the connector is in a second orientation rotationally displaced from said first orientation; and said body further including complementary wing elements adjacent to said split and extending radially therefrom with respect to said central axis;

said wing elements being adapted for being biased together and clamped against a region of said fluid transfer device, thereby applying a compressive force to secure the catheter to the tubular port while preventing said connector from rotating about said central axis.

10. The assembly of claim 9 wherein said connector further comprises means for selectively capturing said wing elements against said flange at said fluid transfer device when said body member is engaged to said fluid transfer device with said aperture being coaxial with and positioned about said tubular extension and said opposed edges of said slit are positioned substantially adjacent to each other.

11. The assembly of claim 10 wherein said fluid transfer device includes capture means including a resilient capture member extending from said fluid transfer device adapted to captively engage said wing elements when said elements are positioned against a reference location on said fluid transfer device.

12. Connector apparatus for coupling an end of a resilient tube about the exterior of a tubular extension of a fluid transfer assembly, said extension extending along a port axis and having an outer diameter a, comprising:

a resilient body member having a substantially cylindrical central aperture extending along a central axis, said aperture having a diameter A, where A is greater than a, said body member including:

A. a slit extending along one side of said central aperture and defined by opposed edges of said body member, B. a hinge region adjacent to said central aperture opposite said slit and extending along a hinge axis, said hinge axis being parallel to said central axis, said hinge region separating said body part into a first portion and a second portion pivotally joined at said hinge region, whereby said first portion is pivotally coupled to said second portion about said hinge axis, C. compression means for receiving external forces to bias said edges of said slit toward each other, and D. bayonet means responsive to coaxial alignment of said port axis and said central axis and to subsequent rotation of not greater than approximately ninety degrees of said first portion of said body member about said central axis toward said second portion of said body member, for selectively engaging said body member to said fluid transfer assembly with said aperture being coaxial with and positioned about said tubular extension.

13. The connector apparatus of claim 12 wherein the nominal inner diameter of said tube is less than a and the nominal outer diameter of said tube is greater than A when said tube is extended to have an inner diameter equal to a, wherein said body member is adapted to captively hold said tube end to said tubular extension when said body part is engaged to said fluid transfer assembly.

14. The connector apparatus of claims 12 or claim 13 wherein the compression means includes a first substantially planar wing element extending radially from said slit edge of said first portion and a second substantially planar wing element extending radially from said slit edge of said second portion.

15. The connector apparatus of claim 14 further comprising in combination with said body member, said fluid transfer assembly, said fluid transfer assembly including means for selectively capturing said wing elements against said fluid transfer assembly when said body member is engaged to said fluid transfer assembly with said aperture being coaxial with and positioned about said tubular extension and said opposed edges of said slit are positioned substantially adjacent to each other.

16. The assembly of claim 15 wherein said fluid transfer device includes capture means including a resilient capture member extending from said fluid transfer device adapted to captively engage said wing elements when said elements are positioned against a reference location on said fluid transfer device.

* * * * *